United States Patent [19]

Watthey

[11] Patent Number: 4,588,746
[45] Date of Patent: May 13, 1986

[54] PROPYLAMINE DERIVATIVES

[75] Inventor: Jeffrey W. H. Watthey, Chappaqua, N.Y.

[73] Assignee: Ciba-Geigy Corporation, Ardsley, N.Y.

[21] Appl. No.: 568,000

[22] Filed: Jan. 4, 1984

Related U.S. Application Data

[63] Continuation-in-part of Ser. No. 415,000, Sep. 7, 1982, abandoned.

[51] Int. Cl.$^4$ .......................................... A61K 31/185
[52] U.S. Cl. ............................... 514/554; 260/501.18; 260/501.19; 514/651; 514/574; 546/236; 560/9; 560/37; 564/304; 564/347; 564/355
[58] Field of Search ................ 564/347; 514/554, 558, 514/651, 574; 260/501.18, 501.19

[56] References Cited

U.S. PATENT DOCUMENTS

| | | | |
|---|---|---|---|
| 3,079,403 | 2/1963 | Weinstack | 564/347 X |
| 3,253,040 | 5/1966 | Potter et al. | 564/347 X |
| 3,676,496 | 7/1972 | Mauvernay et al. | |
| 3,818,000 | 6/1974 | Mauvernay et al. | |
| 4,018,895 | 4/1977 | Molloy et al. | |
| 4,194,009 | 3/1980 | Molloy et al. | |
| 4,207,343 | 6/1980 | Lavagnino et al. | |

FOREIGN PATENT DOCUMENTS

| | | |
|---|---|---|
| 975375 | of 1975 | Canada . |
| 2148001 | 3/1973 | France . |
| 2455571 | of 1981 | France . |
| 1343527 | of 1974 | United Kingdom . |

OTHER PUBLICATIONS

Coll. Czech. Chem. Comm. 46, 1597 (1981).

*Primary Examiner*—Robert V. Hines
*Attorney, Agent, or Firm*—Norbert Gruenfeld

[57] ABSTRACT

Disclosed are e.g. certain novel 2-benzyl-3-(substituted)-phenoxypropylamines, their methods of synthesis and pharmaceutical compositions. Said compounds are useful as potent and centrally active serotonin uptake inhibitors for the treatment of psychotropic disorders, particularly depression.

7 Claims, No Drawings

PROPYLAMINE DERIVATIVES

CROSS-REFERENCE TO RELATED APPLICATION

This is a continuation-in-part of application Ser. No. 415,000 filed Sept. 7, 1982 and now abandoned.

BACKGROUND OF THE INVENTION

Variously substituted 3-aryloxypropylamines are known, e.g. those substituted by phenyl or substituted phenyl at the 1-,2-, or 3-position of the chain.

Protiva et al. in Coll. Czech. Communications 46,597 (1981) reports on certain 3-phenoxy-2-phenylpropylamines.

French patent application 2,148,001 (and the substantially equivalent Canadian 975,375, Belgian 786,450 and British 1,343,527) are directed to compounds claimed to be certain 2-(aryl, aralkynyl, or aralkyl)-3-(aryl or alk)-oxypropylamines active on the cardiovacsular system. Example 60 therein is indicated to have a structure corresponding to 2-benzyl-3-phenoxy-N,N-diethylpropylamine. By repeating the preparation of example 60 of French patent application 2,148,001 using methodology given therein, it has now been found that the product of example 60 actually consists essentially of a compound not having the alleged structure. This compound has instead been assigned the 1-phenoxymethyl-3-phenyl-N,N-diethylpropylamine structure (a 2-phenoxyethylamine derivative).

No other compounds with a 2-benzyl-3-phenoxypropylamine skeleton are known to have been reported in the available literature.

SUMMARY OF THE INVENTION

The present invention relates to certain novel 2-benzyl-3-(substituted)-propylamines of formula I which are surprisingly useful as potent and centrally active serotonin uptake inhibitors.

The foregoing attributes render the compounds of this invention particularly useful when administered alone or in combination to mammals for the treatment of psychotropic disorders, especially depression.

The compounds of the invention may also be useful for the treatment of other central nervous system disorders responsive to brain serotonin modulation, e.g. minimal brain dysfunction, excessive appetite, anxiety, schizophrenia and dementia.

DETAILED DISCLOSURE OF THE INVENTION

In particular the present invention relates to compounds of the general formula I

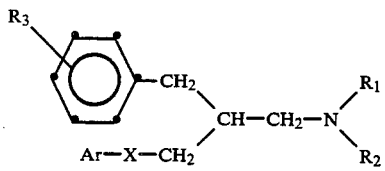

(I)

wherein $R_1$ and $R_2$ independently of the other represent hydrogen or lower alkyl; or $R_1$ and $R_2$ together with the adjacent nitrogen atom represent a five- or six-membered heterocyclic ring or a five- or six-membered heterocyclic ring containing another hetero-atom; $R_3$ represents hydrogen, lower alkyl, lower alkoxy, halogen or trifluoromethyl; Ar represents phenyl substituted by one or two substituents selected from the group consisting of lower alkyl, lower alkoxy, lower alkenyloxy, lower alkynyloxy, lower alkylmercapto, lower alkylsulfinyl, lower alkylsulfonyl, halogen and trifluoromethyl, or by one lower alkylenedioxy on adjacent carbon atoms; and X represents O or S; acid addition salts thereof, particularly pharmaceutically acceptable salts; N-oxides thereof; and N-lower alkyl or N-benzyl quaternary salts thereof; as well as the methods for preparing said compounds; pharmaceutical compositions containing the same; and methods of treating nervous system disorders, e.g. depression, by administration of said compounds and compositions to mammals.

Preferred are the compounds of general formula I, wherein $R_1$ and $R_2$ independently represent hydrogen or lower alkyl; or $R_1$ and $R_2$ together with the adjacent nitrogen atom represent pyrrolidino or piperidino; $R_3$, Ar and X have the meanings given above; and acid addition salts thereof.

Illustrative of the above-cited preferred compounds are compounds represented by general formula I wherein $R_1$ and $R_2$ independently represent hydrogen, methyl or ethyl; $R_3$ represents hydrogen, chloro or trifloromethyl; Ar represents phenyl substituted by one or two substituents selected from the group consisting of methyl, methoxy, allyloxy, methylmercapto, methylsulfinyl, chloro, bromo and trifluoromethyl, or by one methylenedioxy; X represents O or S; and pharmaceutically acceptable acid addition salts thereof.

Preferred are compounds of formula I wherein $R_1$ and $R_2$ independently represent hydrogen or lower alkyl; or $R_1$ and $R_2$ together with the adjacent nitrogen represent piperidino; $R_3$ represents hydrogen, halogen or trifluoromethyl; Ar represents phenyl monosubstituted or disubstituted by identical or different substituents selected from lower alkyl, lower alkoxy, lower alkenyloxy, lower alkylmercapto, lower alkylsulfinyl, lower alkylsulfonyl, halogen and trifluoromethyl; or Ar represents phenyl monosubstituted by lower alkylenedioxy; and X represents O or S; and acid-addition salts thereof.

Of particular interest are the compounds of formula IA

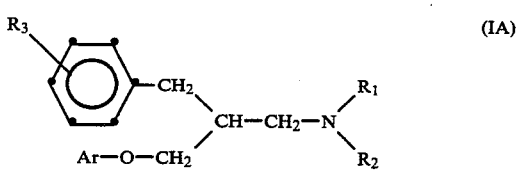

(IA)

wherein $R_1$ and $R_2$ independently represent hydrogen or lower alkyl; $R_3$ represents hydrogen, halogen or trifluoromethyl; Ar represents phenyl monosubstituted or disubstituted by identical or different substituents selected from lower alkyl, lower alkoxy, lower alkenyloxy, lower alkylmercapto, lower alkylsulfinyl, lower alkylsulfonyl, halogen and trifluoromethyl; and the acid-addition salts thereof.

Highly preferred are the compounds of formula IA wherein $R_1$ represents hydrogen or alkyl of 1–4 carbons; $R_2$ represents alkyl of 1–4 carbons; $R_3$ represents hydrogen or chloro; Ar represents phenyl mono-substituted by alkoxy of 1–4 carbons, alkyl of 1–4 carbons, alkylmercapto of 1–4 carbons, chloro, or trifluoromethyl; and the pharmaceutically acceptable salts thereof.

Another preferred embodiment of the invention is represented by compounds of formula IA wherein $R_1$ represents hydrogen; $R_2$ represents alkyl of 1-4 carbons; $R_3$ represents hydrogen or chloro; Ar represents phenyl monosubstituted by alkoxy of 1-4 carbons, alkyl of 1-4 carbons, alkylmercapto of 1-4 carbons, chloro or trifluoromethyl; and the pharmaceutically acceptable salts thereof.

Most preferred are said compounds of formula IA wherein Ar represents phenyl monosubstituted by alkylmercapto of 1-4 carbons or trifluoromethyl.

For the compounds of formula IA within all the embodiments described above, Ar advantageously represents phenyl di- or mono-substituted at the 3- and/or 4-position of the phenyl ring by groups listed above.

Illustrative of the preferred compounds of formula IA, are said compounds wherein $R_1$ represents hydrogen or methyl; $R_2$ represents methyl; $R_3$ represents hydrogen, or chloro at the 3- or 4-position advantageously at the 3-position; Ar represents phenyl mono-substituted by methoxy, methyl, methylmercapto, chloro, or trifluoromethyl; or a pharmaceutically acceptable salt thereof. Preferred in turn are the said compounds wherein Ar represents phenyl substituted at the 3- or 4-position, advantageously at the 4-position, by methoxy, methylmercapto or trifluoromethyl, advantageously by methylmercapto or trifluoromethyl. A more preferred embodiment is represented by compounds wherein $R_3$ represents hydrogen and Ar represents 4-trifluoromethylphenyl.

The preferred compounds of the invention are highly potent as well as selective brain neuronal serotonin uptake inhibitors. At effective serotonin uptake inhibitory doses or higher, such compounds exhibit no significant norepinephrine uptake inhibitory activity.

A preferred selective brain neuronal serotonin uptake inhibitor is N-methyl-2-benzyl-3-(4-trifluoromethylphenoxy)-propylamine and pharmaceutically acceptable salts thereof.

The general definitions used herein have the following meanings within the scope of the present invention.

The term "lower" referred to above and hereinafter in connection with organic radicals or compounds respectively defines such with up to and including 7, preferably up to and including 4 and advantageously one or two carbon atoms.

A lower alkyl group preferably contains 1-4 carbon atoms and represents for example ethyl, propyl, butyl or advantageously methyl.

Lower alkoxy is preferably ethoxy, propoxy, isopropoxy or advantageously methoxy.

Lower alkylthio is preferably ethylthio, propylthio or advantageously methylthio.

Lower alkylsulfinyl is preferably ethylsulfinyl, propylsulfinyl or advantageously methylsulfinyl.

Lower alkylsulfonyl is preferably ethylsulfonyl, propylsulfonyl or advantageously methylsulfonyl.

An alkenyl group, as such or as present in e.g. alkenyloxy, represents straight chain or branched alkenyl preferably up to 7 carbon atoms, advantageously up to and including 4 carbon atoms, e.g., 2-propenyl (allyl), 2-butenyl, 2-methyl-2-propenyl, 2-methyl-2-butenyl and the like.

An alknynyl group, as such or as present in e.g. alkynyloxy, represents straight chain or branched alkynyl preferably up to 7 carbon atoms, advantageously up to and including 4 carbon atoms, e.g., 2-propynyl (propargyl), 2-butynyl, 2-pentynyl and the like.

Halogen is preferably chloro, but may also be bromo, iodo or fluoro.

When $R_1$ and $R_2$ combined with the adjacent nitrogen to which they are attached in formula I represent a five- or six-membered heterocyclic ring, the ring may be devoid of or may contain an additional hetero atom. Five- and six-membered heterocyclic ring moieties devoid of an additional hetero atom are preferably pyrrolidino and piperidino. Five- and six-membered heterocyclic ring moieties containing an additional hetero atom include those wherein the additional hetero group is NH, N-lower alkyl, O or S. Representative moieties are preferably pyrazolidino, isooxazolidino, and advantageously morpholino, thiomorpholino, piperazino and N-lower alkylpiperazino.

Pharmaceutically acceptable salts are acid addition salts, which are preferably such of therapeutically acceptable inorganic or organic acids, such as strong mineral acids, for example hydrohalic, e.g. hydrochloric or hydrobromic acid; sulfuric, phosphoric or nitric acid; aliphatic or aromatic carboxylic or sulfonic acids, e.g. formic, acetic, propionic, oxalic, succinic, glycolic, lactic, malic, tartaric, gluconic, citric, ascorbic, maleic, fumaric, pyruvic, phenylacetic, benzoic, 4-aminobenzoic, anthranilic, 4-hydroxybenzoic, salicylic, 4-aminosalicylic, pamoic, nicotinic; methanesulfonic, ethanesulfonic, hydroxyethanesulfonic, benzenesulfonic, p-toluenesulfonic, naphthalenesulfonic, sulfanilic or cyclohexylsulfamic acid.

Acid addition salts, such as of other strong inorganic or organic acids, e.g., perchloric or picric acid can also be used for the isolation, purification and characterization of the compounds of formula I.

The compounds of the invention exhibit valuable pharmacological properties, e.g. particularly central nervous system regulatory, specifically effects indicative of antidepressant activity, by inter alia selectively inhibiting brain neuronal serotonin (also designated as 5-hydroxytryptamine or 5-HT) uptake. Compounds of the invention are also inhibitors of neuronal uptake of norepinephrine (NE).

The preferred compounds of the invention are more potent as serotonin uptake inhibitors. They exhibit no or insignificant norepinephrine uptake inhibition activity at effective serotonin uptake inhibitory doses.

Said effects are demonstrable by in vitro and in vivo tests using advantageously mammals, e.g. mice, rats, guinea pigs, rabbits or monkeys as test subjects. Said compounds can be applied to them enterally or parenterally, advantageously orally, or subcutaneously, intravenously or intraperitoneally, for example, within gelatin capsules or in the form of starchy suspensions or aqueous solutions or suspensions respectively. The applied dosage may range between about 0.1 and 100 mg/kg/day, preferably between about 1 and 50 mg/kg/day, advantageously between about 5 and 30 mg/kg/day.

The inhibition of serotonin (5-HT) uptake indicative of potential antidepressant activity is determined in rat midbrain synaptosomes in vitro as follows:

Synaptosomes from the rat midbrain-diencephalon region are prepared and the uptake of $^3$H-5-HT measured as described by Baumann and Maitre, Naunyn-Schmiedeberg's Arch. Pharmacol. 300, 31 (1977). The concentration of 5-HT in the incubation medium is $2.5 \times 10^{-9}$M, and the incubation period is 10 minutes. The concentration of a compound of this invention required to inhibit serotonin uptake by 50%, i.e. the IC$_{50}$, is determined.

Illustrative of the invention, N,N-dimethyl-2-benzyl-3-(4-methylmercaptophenoxy)-propylamine oxalate, N,N-dimethyl-2-benzyl-3-(4-trifluoromethylphenoxy)-propylamine oxalate and N-methyl-2-benzyl-3-(4-trifluoromethylphenoxy)-propylamine oxalate inhibit the uptake of $^3$H-5-HT into rat midbrain synaptosomes with IC$_{50}$ values of about $3 \times 10^{-8}$M, $1.5 \times 10^{-8}$M and $1 \times 10^{-8}$M respectively.

The inhibition of norepinephrine (NE) uptake is determined in rat midbrain synaptosomes in vitro as follows:

Synaptosomes from the rat midbrain-diencephalon region are prepared and the uptake of $^3$H-NE is measured as described by Baumann and Maitre, Naunyn-Schmiedeberg's Arch. Pharmacol. 300, 31 (1977). The concentration of NE in the incubation medium is $1 \times 10^{-8}$M, and the incubation period is 20 minutes. The concentration required to inhibit norepinephrine uptake by 50%, i.e. the IC$_{50}$, is determined.

N,N-dimethyl-2-benzyl-3-(4-methylmercaptophenoxy)-propylamine oxalate, N,N-dimethyl-2-benzyl-3-(4-trifluoromethylphenoxy)-propylamine oxalate and N-methyl-2-benzyl-3-(4-trifluoromethylphenoxy)-propylamine oxalate inhibit the uptake of $^3$H-NE into rat midbrain synaptosomes with IC$_{50}$ values of about $5 \times 10^{-7}$M, $3 \times 10^{-6}$M and $2 \times 10^{-6}$M respectively.

Serotonin (5-HT) uptake inhibition is also determined in rats pretreated with compounds of the instant invention.

Illustrative of the invention, N,N-dimethyl-2-benzyl-3-(4-methylmercaptophenoxy)-propylamine oxalate and N,N-dimethyl-2-benzyl-3-(4-trifluoromethylphenoxy)-propylamine oxalate at an oral dose of 30 mg/kg p.o show about 80% and 60% inhibition respectively of $^3$H-5HT uptake. N-Methyl-2-benzyl-3-(4-trifluoromethylphenoxy)-propylamine oxalate gives about a 50% inhibition of $^3$H-5HT uptake at a dose of 10 mg/kg p.o.

The serotonin uptake inhibiting or serotonin activating properties of the compounds of the invention are indicative of antidepressant properties as determined by the reversal of reserpine-induced ptosis (i.e. contraction of the eyelid) in the rabbit.

Rabbits are injected intravenously with 2 mg/kg reserpine 90 minutes before the i.v. infusion of 0.2% drug solution into the ear vein according to the method of J. Mizoule et al. (J. Pharmacol., 8, 3, 269–285, 1977). The complete opening of the eye-lids is taken as a criterion for reversal of the reserpine-induced ptosis.

The results are expressed in terms of the mean dose of test compound inducing complete opening of the eye-lids in reserpine treated rabbits.

Illustrative of the invention, N,N-dimethyl-2-benzyl-3-(4-methylmercaptophenoxy)-propylamine oxalate, N,N-dimethyl-2-benzyl-3-(4-trifluoromethylphenoxy)-propylamine oxalate and N-methyl-2-benzyl-3-(4-trifluoromethylphenoxy)-propylamine oxalate induce opening of the eyelids in reserpine treated rabbits at a dose of about 7.7, 12.6 and 12.9 mg/kg i.v. respectively.

The inhibition of the serotonin depleting effect of 3-hydroxy-4-methyl-α-ethylphenethylamine (H 75/12) in rat brain serves as an indirect indication of serotonin uptake inhibitory activity. (Carlsson, Corrodi, Fuxe and Hoekfelt, Europ. J. Pharmacol. 5, 357, 1969). A diminution of serotonin release by H 75/12 is considered to be due to a serotonin uptake inhibitory effect of the test compound. The compound to be tested is administered orally 30 minutes before H 75/12 (25 mg/kg s.c.) and the animals are decapitated 4 hours thereafter. The brains are immediately taken out and serotonin is determined as described above. The ED$_{50}$ represents the dose of the test compound inhibiting the seretonin-depleting effect of H75/12 by 50%.

Similarly the inhibition of the norepinephrine depleting effect of 3-hydroxy-4-methyl-α-methylphenethylamine (H77/77) in rat brain serves as an indirect indication of norepinephrine uptake inhibitory activity (Carlsson, Corrodi, Fuxe and Hoekfelt, Europ. J. Pharmacol. 5, 367, 1969). A diminution of norepinephrine release by H 77/77 is considered to be due to a norepinephrine-uptake inhibitory effect of the test compound. The compound to be tested is administered orally 30 minutes before H 77/77 (6.25 mg/kg s.c.) and the animals are decapitated 4 hours thereafter. The brains are immediately taken out and norepinephrine is determined as described above.

Illustrative of the serotonin uptake inhibiting effect of the compounds of the invention, the ED$_{50}$ values in the above H 75/12 test for N,N-dimethyl-2-(3-chlorobenzyl)-3-(4-methylmercaptophenoxy)-propylamine oxalate and N-methyl-2-benzyl-3-(4-trifluoromethylphenoxy)-propylamine oxalate are about 1.4 and 1.8 mg/kg p.o. respectively. The ED$_{50}$ values for N,N-dimethyl-2-benzyl-3-(4-methylmercaptophenoxy)-propylamine oxalate and N,N-dimethyl-2-benzyl-3-(4-trifluoromethylphenoxy)-propylamine oxalate are about 2.3 and 4.5 mg/kg p.o. respectively.

In contrast thereto, none of the four above-cited compounds, at a dose of 100 mg/kg p.o in the rat, inhibited the norepinephrine depleting effect of H 77/77 as determined in the above described H 77/77 test.

Compounds of formula I according to the invention can be prepared by synthetic procedures which are per se known to those skilled in the art.

In particular, compounds of formula I are prepared by (a) condensing a compound of the formula

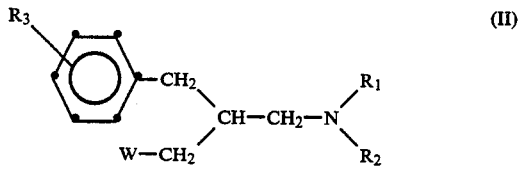

(II)

or an acid addition salt thereof, with a compound of the formula

Ar—Y  (III)

wherein R$_1$, R$_2$, R$_3$ and Ar have the meanings given hereinabove, and one of the symbols W and Y represents a group —X—H in which X has the meaning given hereinabove or a metal salt thereof, and the other one represents the group —X—H in a reactive esterified form thereof; or (b) condensing an amine of the formula

(IV)

or an acid addition salt thereof, with a compound of the formula

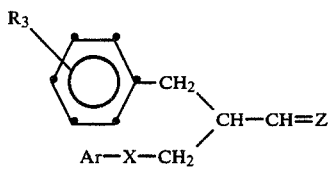

(V)

(c) reducing a compound structurally analogous to a compound of formula I defined hereinabove, wherein an oxo group is present on at least one carbon atom adjacent to the amino nitrogen; or (d) saturating (a) multiple bond(s) in a compound structurally analogous to the compound of formula I defined hereinabove, wherein one or two double bonds is (are) present in the aliphatic portion of the molecule inclusive of the amino group; or (e) removing the radical $R_o$ from a compound of the formula,

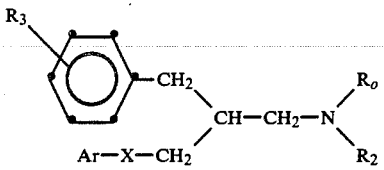

(VI)

wherein $R^2$, $R^3$, X and Ar have the meanings given hereinabove and $R_o$ is an amino protecting group, to obtain a compound of formula I in which $R_1$ is hydrogen;

(f) reducing a compound of the formula

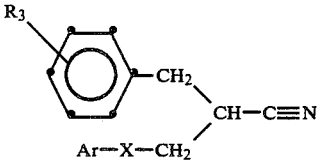

(VII)

wherein $R_3$, X and Ar have the meanigs given hereinabove to obtain a compound of formula I wherein $R_1$ and $R_2$ are hydrogen; and, optionally, (g) converting a resulting compound of formula I defined above into another compound of formula I defined above, and optionally, (h) converting any resulting compound of formula I defined hereinabove into an acid addition salt thereof or liberating the free base of a resulting acid addition salt thereof; and optionally, (i) isolating in enriched form from a mixture of stereoisomeric forms of a resulting compound of formula I defined hereinabove, an optical isomer which has a specific configuration with respect to at least one center of chirality.

The condensation according to process (a) is carried out as described below.

The group —X—H is a hydroxyl or a mercapto (thiol) group. A metal salt of this group is derived preferably from an alkali metal (e.g. potassium, lithium or, especially, sodium) or, in the case of mercapto, also from uni- or bivalent copper.

The condensation according to process (a) is carried out advantageously by making use of a reactive esterified hydroxyl or thiol group derived from a carbodiimide, i.e., that being represented as an O- (or S-)derivative of an N,N'-disubstituted isourea (or isothiourea) and having the characteristic grouping

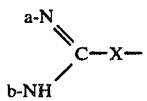

in which X has the meanings given hereinabove and a and b are optionally substituted hydrocarbyl radicals e.g. especially cyclohexyl. Advantageously, the reactive esters of this type are obtained and reacted in situ, e.g. by heating a mixture of an esterifying reactant, especially a N,N'-disubstituted derivative of carbodiimide, e.g. especially N,N'-dicyclohexyl carbodiimide and the starting materials of formulae II and III, in which both W and Y are in the form of a free hydroxyl or thiol group respectively. Alternatively, one of the starting materials may be heated advantageously at a temperature ranging from 50 to 200 C., with the N,N'-substituted carbodiimide in the presence of cuprous chloride to form the isourea or isothiourea derivative. Subsequently the second starting material is added and heating is continued to form the product.

The condensation according to process (a) may also be carried out in a more conventional manner. A reactive esterified form of the group —X—H is thus preferably one in which the hydroxyl or thiol group, respectively, is esterified with a strong organic acid, e.g. an aliphatic or aromatic sulfonic acid (such as a lower alkanesulfonic acid, especially methanesulfonic, trifluoromethanesulfonic and ethanesulfonic acid, or an arylsulfonic acid, especially benzenesulfonic, p-toluenesulfonic, p-bromobenzenesulfonic and p-nitrobenzenesulfonic acid) or with a strong inorganic acid, such as, especially, sulfuric acid or a hydrohalic acid, e.g., hydrobromic, hydriodic or, preferably, hydrochloric, and if attached to the residue Ar, most preferably hydrofluoric acid. If the symbol W or Y specifically represents the group —X—H reactively esterified with a hydrohalic acid, it represents, in fact, the corresponding halogen atom, i.e. a bromine, iodine or, preferably chlorine or, especially in connection with the residue Ar a fluorine atom.

In the case of a substrate ArY wherein Y represents halogen, especially fluorine, an activating group, e.g. a trifluoromethyl, alkylsulfonyl or alkylsulfinyl group, is advantageously located ortho or para to the halogen atom. An especially suitable substrate as p-fluorobenzotrifluoride. When the condensation according to process (a) is carried out as described above, temperatures ranging between about 0° C. up to the boiling temperature of the reaction mixture, preferably temperatures between room temperature and about 100° C. are employed. The reaction takes place advantageously in the presence of a solvent which is inert with respect to the reactants, such as especially an acyclic or cyclic ether (e.g. diethyl ether, 1,2-dimethoxyethane, dioxane or tetrahydrofuran) and, in particular, low-molecular-weight tertiary amide (e.g. N,N-dimethylformamide, N,N-dimethylacetamide, N-methylpyrrolidone, N-ethylpiperidone and hexamethylphosphoric acid triamide). Advantageously, if a strong acid is liberated during the condensation, it is bound by the addition of an acid-binding agent, e.g. a conventional inorganic acid-scavenger such as an alkali metal carbonate or hydroxide or preferably, of a very strong base, such as an alkali metal hydride (e.g. sodium or potassium hydride), alkoxide (e.g. sodium methoxide or ethoxide, potassium tert-butoxide) or amide (e.g. lithium diisopropylamide). Starting with a compound of formula II, wherein W is halogen (preferably chlorine), it is advantageous to convert first the corresponding reactant of formula III, i.e. in this case a phenol, into a corresponding metal phenoxide, especially an alkali-metal phenoxide (e.g. a sodium phenoxide) by the action of an equivalent amount of sodium hydride in a polar aprotic solvent, e.g. one of those mentioned above, and to carry out the condensation with this salt. In carrying out the condensation with starting materials of formulae II and III, in which the reactive esterified hydroxyl group is formed in situ by the action of an N,N'-disubstituted carbodiimide such as N,N'-dicyclohexylcarbodiimide, conventional conditions for this condensation are used as well-known in the art.

Starting materials of formula III are, in general, known compounds, or if unknown, they are easily accessible in a manner which is analogous to the preparation of known compounds.

Starting materials of formula II, which are generally new, are accessible by conventional, in themselves known processes of organic synthesis. For example, a lower alkyl α-benzylacrylate of the formula VIII,

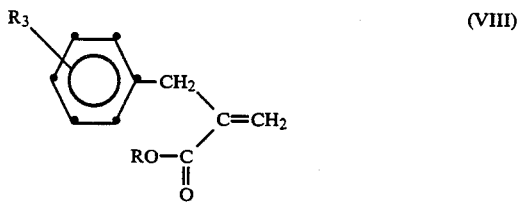

wherein $R_3$ has the meaning given hereinabove and R is a lower alkyl [for preparation, see R. B. Miller and B. F. Smith, Synth. Commun. 3, 359 (1973)], is condensed with a secondary amine of formula IV as defined hereinabove in a lower alkanol under the general conditions of a Michael addition, and the resulting lower alkyl α-benzyl-β-aminopropionate of the formula

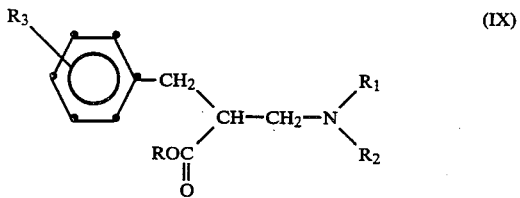

in which $R_1$, $R_2$ and $R_3$ have the meanings given hereinabove and R is a lower alkyl, is reduced with a complex hydride, preferably lithium aluminum hydride or an equivalent carbonyl-reducing agent, to the corresponding alcohol, i.e. a compound of formula II, in which W is hydroxyl. If desired, this hydroxyl can be converted into a reactive esterified form thereof by conventional means, e.g. for the preparation of a preferred chloride (W=Cl) by treatment with thionyl chloride, phosphorus trichloride, phosphorus oxychloride or a similar reagent.

Process (b) is carried out in the conventional manner well-known in the art as alkylation of amines. In the starting materials of formula V, the group Z (replaceable by amino) can represent especially a hydrogen atom together with a reactive esterified hydroxyl group, or the oxo group. In the first case, the amino alkylation proceeds under the general conditions of substitutive alkylation of amines, in the second case general conditions of reductive alkylation of amines are applicable.

In the case of substitutive alkylation of the amine of formula IV, the reactive esterified hydroxyl group in a compound of formula V is similar to that used in process (a), especially a hydroxyl group esterified with a strong organic acid, e.g. an aliphatic or aromatic sulfonic acid (such as a lower alkanesulfonic acid, especially methanesulfonic, trifluoromethanesulfonic acid, benzenesulfonic, p-toluenesulfonic, p-bromobenzenesulfonic and p-nitrobenzenesulfonic acid) or esterified with a strong inorganic acid, such as, especially, sulfuric acid, or a hydrohalic acid, such as hydrochloric or, most preferably, hydriodic or hydrobromic acid. The alkylation is carried out preferably under similar conditions and with the same solvents as in process (a), however, halogenated alkanes, e.g. chloroform and methylene chloride, are also useful solvents. Usually also milder acid-scavengers than in process (a) are employed, especially organic quarternary bases (e.g. a tetrabutylammonium salt) or organic tertiary bases, e.g. triethylamine, N-ethylpiperidine, benzyldiethylamine, pyridine or quinoline.

The condensation according to process (b) can also be carried out under the conditions of reductive alkylation of amines in the manner generally known and used in the art. A compound of formula V, in which Z represents oxo and X, Ar and $R_3$ have the meanings given hereinabove, is used as the alkylating agent and is reacted with the starting amine IV and, simultaneously or in a subsequent step, with a reducing agent. Among reducing agents which are used simultaneously with the alkylating agent, mention should be made of complex metal hydrides such as sodium cyanoborohydride; among reducing agents used predominatly in a separate subsequent operation, mention should be made of diborane and complex metal hydrides, such as sodium borohydride and sodium cyanoborohydride, which are applied advantageously to the primary reaction mixture without isolating an intermediate. In this case, the alkylation is carried out advantageously in an organic solvent inert to the reducing agent, such as an aliphatic or cyclic ether (e.g. diethyl ether, diisoproyl ether, 1,2-dimethoxyethane, dioxane or tetrahydrofuran) or an aliphatic alcohol (such as methanol, ethanol, isopropyl alcohol, glycol, glycol monomethyl ether or diethyleneglycol), preferably at about 0°–80° C. However, a principal reducing agent which can be used both simultaneously and subsequently, is hydrogen, especially catalytically activated hydrogen. The catalysts are those conventionally used as hydrogenation catalysts, i.e. preferably those of the class of precious metal (such as palladium, platinum and rhodium) on a carrier (such as carbon black, calcium carbonate, aluminum oxide or barium sulfate), in a finely dispersed suspension without carrier or, in form of complexes, in a homogeneous phase. Also, finely dispersed transition metals such as Raney nickel, are very suitable catalysts for the reductive alkylation. The specific reaction conditions depend, to a large extent, on the particular hydrogenation catalyst and its specific activity, and do not differ from those generally known for hydrogenation. Temperatures ranging from room temperature to about 150° C., and pressures of hydrogen ranging from atmospheric pressure to about 300 atmospheres are applicable according to the standard procedures of the art. In addition to the inert solvents which are mentioned above in connection with the hydride reduction, low-molecular amides, especially tertiary amides (such as N,N-dimethylformamide, N,N-dimethylacetamide, N-methylpyrrolidone, N-ethylpiperidone, and hexamethylphosphoric acid triamide), also formamide and acetamide can be used as suitable solvents. Special measures have to be taken with starting materials of formula V in which X represents S; since most hydrogenation catalysts are deactivated by sulfur compounds, other reducing agents (such as complex metal hydrodes mentioned hereinabove, especially sodium cyanoborohydride) are preferred in this case.

The starting amines of formula IV are known compounds. The novel starting materials of formula V can be otained according to conventional synthetic methods, e.g. from a compound of formula X,

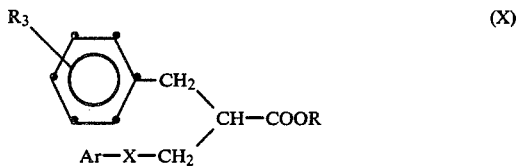

wherein $R_3$, X and Ar have the meanings given hereinabove, and R represents hydrogen or lower alkyl, to give compounds of formula V wherein Z represents oxo or X represents hydrogen together with reactive esterified hydroxy.

Intermediates of formula X are advantageously prepared by condensing a compound of formula VIII with a compound of formula Ar—XH wherein X represents O or S, or e.g. an alkali metal salt thereof, under standard conditions of Michael addition. Compounds of formula X are reduced to compounds of formula V wherein Z represents hydrogen together with a hydroxyl group according to well-known conventional procedures, especially with complex metal hydrides under standard conditions. Reduction of compounds of formula X with e.g. diisobutyl aluminum hydride also yields the aldehydes having formula V wherein Z represents oxo. Alternatively, the aldehydes may also be obtained by oxidation of the above compounds of formula V, wherein Z represents hydrogen together with a hydroxyl group, with e.g. pyridinium dichromate in methylene chloride. If starting materials are required in which Z is hydrogen together with a reactive esterified hydroxyl group, the free hydroxyl group is converted into its reactive esterified form by conventional processes used for the esterification with strong acids, e.g. for the halides, by reacting with conventional halogenating agents mentioned hereinabove in connection with the preparation of analogous starting materials of formula II.

Process (c) can also be carried out in the manner generally known for the reduction of amides to amines. In the starting materials, one or two carbon atoms adjacent to the nitrogen atom can carry an oxo group forming an amide or imide grouping. Starting materials for this process are represented by the formula

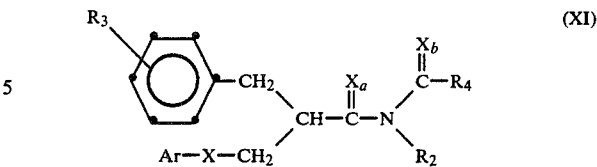

in which X, Ar, $R_2$ and $R_3$ have the meanings given hereinabove, $R_4$ is hydrogen or lower alkyl of one less carbon atom than $R_1$; or $R_2$ and $R_4$ are joined together to form a five- or six-membered heterocyclic ring; and one of the symbols $X_a$ and $X_b$ represents oxo and the other one represents oxo or two hydrogen atoms. The reduction is carried out with a conventional appropriate reducing agent, e.g. preferably, a complex metal hydride such lithium aluminum hydride or borane.

Starting materials of formula XI are new and can be prepared by processes which are in themselves known. Thus, compounds of formula XI wherein $X_a$ is oxo and $X_b$ represents two hydrogens are prepared by the simple amidation of an intermediate of formula X specified hereinabove with an amine of formula IV specified hereinabove. Starting materials of formula XI, in which $X_a$ represents two hydrogens and $X_b$ is oxo, can be obtained e.g. by acylation, of a compound of formula I in which at least one of $R_1$ and $R_2$ represents hydrogen, with a reactive derivative of an alkanoic acid, e.g. acetyl chloride.

Process (d) can also be performed in a manner per se known, and under conventional conditions. The double bond in the starting materials for process (e) can be located either between the nitrogen atom and one adjacent carbon atom or between two carbon atoms. Thus, a carbon bond may be positioned between the nitrogen atom and any one of the neighbouring carbon atoms, and an additional carbon-to-carbon double bond can be placed on the central carbon atom. Also, starting materials can be used having solely a carbon-to-carbon double bond, which joins the central carbon atom to any of the three adjacent carbon atoms. Starting materials for process (e) are represented by the formula $XII_a$

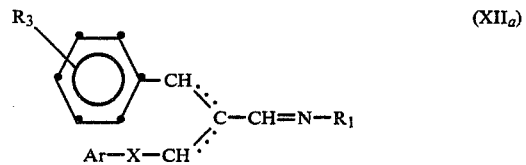

wherein $R_1$, $R_3$, Ar and X have the meanings given hereinabove, and the dotted lines indicate one optionally present double bond, or by the formula $XII_b$

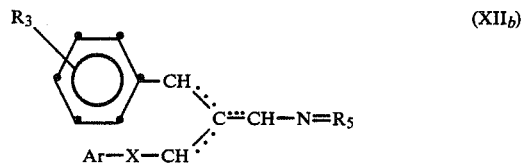

wherein $R_3$, Ar and X have the meanings given hereinabove, $R_5$ represents a lower alkylidene residue and the dotted lines indicate one optionally present double bond, or by the formula XIII

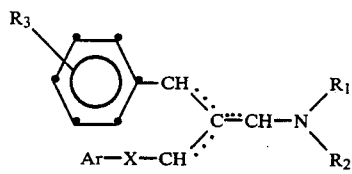

(XIII)

wherein $R_1$, $R_2$, $R_3$, Ar and X have the meanings given hereinabove and the dotted lines indicate one double bond.

Process (e) can be carried out in a manner generally known in the art, especially under conditions for removing amino-protecting groups. Suitable protecting groups, as well as procedures for their introduction and removal are well known in the art, being elaborated in great detail in particular as general methods for the synthesis of peptides; e.g., see Houben-Weyl: Methoden der Organishen Chemie; 4th edition, vol. 15/I and II, E. Wunsch (editor): Synthese von Peptiden (Georg Thieme Verlag, Stuttgart, 1974).

Suitable as amino-protecting groups ($R_o$) are especially amino-protecting groups that can be removed by reduction, for example, especially the benzyl or benzyloxycarbonyl groups which may be substituted in the aromatic moiety by halogen, lower alkoxy, lower alkyl radicals and, especially, by nitro groups, or alternatively the amino protecting group is isonicotinyloxycarbonyl.

The benzyl, the benzyloxycarbonyl and isonicotinyloxycarbonyl protecting groups are in general smoothly removed by hydrogenolysis, especially by hydrogenation over a precious metal catalyst in a well-established manner. Those groups that contain isonicotinyl radicals (for example isonicotinyloxycarbonyl) and, especially, substituted benzyl radicals especially 4-nitrobenzyl radicals of any kind, are preferably removed by reduction with zinc, usually in the presence of an acid, preferably acetic acid, and with or without the addition of an inert organic solvent, usually at room temperature.

It is also possible to use $R_o$ groups that can be removed by acidolysis, such as the tert-butoxycarbonyl groups and analogous groups as well as those of the aralkyl type, such as benzhydryl, di-(4-methoxy)-benzhydryl and triphenylmethyl (trityl), or certain aralkoxycarbonyl groups of the 2-(p-biphenylyl)-2-propoxycarbonyl type, which are described in Swiss Patent Specification No. 509 266. The removal of a protecting group by acid hydrolysis (acidolysis) is carried out in the case of groups of the tert-butyl type by means of such acids as hydrogen chloride, hydrogen fluoride or trifluoroacetic acid, and in the case of acid-sensistive protecting groups chiefly by means of a lower aliphatic carboxylic acid, such as formic acid and/or acetic acid, in the presence of water, and, optionally, a polyhalogenated lower alkanol or lower alkanone, such as 1,1,1,3,3,3-hexafluoropropan-2-ol or hexafluoroacetone. In this manner it is possible, for example, for an N-trityl group to be removed by an organic acid, such as formic acid, acetic acid, chloroacetic acid or trifluoroacetic acid, in aqueous or absolute trifluoroethanol as solvent (cf. German Offenlegungschrift DT 2 346 147) or by aqueous acetic acid; for the tert-butoxycarbonyl group to be removed by trifluoroacetic acid or hydrochloric acid; and for the 2-(p-biphenylyl)-isopropoxycarbonyl group to be removed by aqueous acetic acid or, for example, by a mixture of glacial acetic acid, formic acid (82.8% strength) and water (7:1:2), or in accordance with the process in DT 2 346 147. An advantageous amino-protecting group $R_o$ is also the ethoxycarbonyl group which carries in the β-position a silyl group substituted by three hydrocarbon radicals, such as triphenylsilyl, dimethylbutylsilyl or especially, trimethylsilyl. A β-(trihydrocarbylsilyl)-ethoxycarbonyl group of this type, such as a β-(trilower alkylsilyl)-ethoxycarbonyl group, for example, especially β-(trimethylsilyl)-ethoxycarbonyl, forms with the amino group to be protected a corresponding β-trihydrocarbylsilyl-ethoxycarbonylamino group (for example the β-trimethylsilylethoxycarbonylamino group), and is preferably removed by fluoride ion-yielding reagents, for example fluorides of quaternary organic bases, such as tetraethylammonium fluoride.

The starting materials for process (e) i.e. the compounds of formula VI specified above, are new. They are prepared in a manner described in particular hereinabove in previous processes, the only difference being that starting materials are used in which the nitrogen of the group —$NR_1R_2$ bears the amino-protecting group $R_o$ in place of the radical $R_1$.

Process (f) is carried out by well-known hydrogenation procedures for the reduction of nitriles, e.g. in the presence of ammonia, or by treatment with a simple or complex metal hydride, such as alane.

The starting materials are advantageously accessible by condensation of an α-benzylacrylonitrile of formula XIV

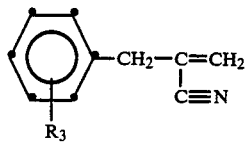

(XIV)

wherein $R_3$ has meaning as previously defined, with a compound of formula ArXH wherein X represents O or S, or e.g. an alkali metal derivative thereof, under standard condition of a Michael addition.

The compounds of the invention obtained by any of the methods described above can be converted into each other according to conventional methods known to the art, and e.g. as illustrated herein.

Compounds of formula I wherein $R_1$ and/or $R_2$ represents(s) hydrogen, may be converted to the compound of formula I wherein $R_1$ and/or $R_2$ represent(s) lower alkyl, by reaction with a reactive esterified lower alkanol, e.g. with a lower alkyl halide, thereby preferably isolating the resulting compound of formula I as the corresponding acid-addition salt, or by reductive alkylation, e.g. with formaldehyde and formic acid to yield the compound of formula I wherein $R_1$ and/or $R_2$ represents methyl.

Compounds of formula I wherein $R_1$ and $R_2$ represent lower alkyl, advantageously wherein $R_1$ and $R_2$ represent methyl, can be converted to compounds of formula I wherein $R_1$ or $R_2$ represent hydrogen by catalytic air oxidation, e.g. with palladium or charcoal using an alcohol such as methanol as the solvent, preferably at room temperature, or by reacting with lower alkyl haloformates, e.g. ethyl chloroformate, to yield N-acyl derivatives which, in turn, may be hydrolyzed to said unsubstituted compounds, those with $R_1$ or $R_2=H$, for example with a base, such as an alkali metal hydroxide, e.g. an aqueous or hydroalcoholic solution of sodium hydroxide.

Compounds of formula I wherein $R_1$ and/or $R_2$ is methyl can be prepared by reacting the corresponding compounds of formula I wherein $R_1$ and/or $R_2$ represents hydrogen with lower alkyl- or phenyl lower alkylhaloformates, such as ethyl chloroformate, to obtain compounds of formula I wherein $R_1$ or $R_2$ is alkoxycarbonyl or phenylalkyloxy-carbonyl, and reducing said acyl derivatives with simple or complex light metal hydrides such as lithium aluminum hydride, sodium tri-t-butoxy or bis-(2-methoxyethoxy) aluminum hydride.

Unsaturated compounds, such as those bearing as alkenyl or alkynyl radical, may be hydrogenated with catalytically activated hydrogen to obtain compounds of formula I or intermediates bearing the corresponding alkyl radical.

With reference to the above reactions, it may be advantageous to appropriately protect the potentially reactive, e.g. amino, carboxy or other interfering substituents in accordance with protective techniques well known to the art, e.g. as illustrated below, such that interfering reactions are avoided, by protecting such substituents prior to the desired reaction and subsequently, if necessary removing the protective groups to obtain the desired compounds, e.g. of formula I, or intermediates.

For instance, a free basic amino group, the group $—NR_1R_2$ bearing at least one hydrogen or nitrogen, may be protected in the form of easily cleaved amides, e.g. as acyl derivatives such as the benzyloxycarbonyl (carbobenzyloxy) or the t-butyloxycarbonyl derivatives, or any other easily removable N-protecting group as previously described.

Similarly a carboxy group may be protected in the form of an easily cleaved ester, e.g. the benzyl ester, the t-butyl ester, and the like as commonly used.

In a resulting protected compound of formula I or intermediate, in which one or more of the functional groups are protected, the protected functional groups, e.g. amino or carboxy groups can be liberated, in a manner, known per se, e.g. by means of solvolysis, especially hydrolysis with acid, or by means of reduction, especially hydrogenolysis.

The above-mentioned reactions are carried out according to standard methods, in the presence or absence of diluents, preferably such as are inert to the reagents and are solvents thereof, of catalysts, condensing or said other agents respectively and/or inert atmospheres, preferably near the boiling point of the solvents used, at atmospheric or superatmospheric pressure.

The invention further includes any variant of the present processes, in which an intermediate product obtainable at any stage thereof is used as starting material and the remaining steps are carried out, or the process is discontinued at any stage thereof, or in which the starting materials are formed under the reaction conditions or in which the reaction components are used in the form of their salts or optically pure antipodes. Whenever desirable, the above processes are carried out after first suitably protecting any potentially interfering reactive functional groups, as illustrated above and in the examples herein.

Advantageously, those starting materials should be used in said reactions, that lead to the formation of those compounds indicated above as being especially preferred.

The invention also relates to novel starting materials and processes for their manufacture.

Depending on the choice of starting materials and methods, the new compounds may be in the form of one of the possible isomers or mixtures thereof, for example, as pure geometric isomers (cis or trans), as pure optical isomers (as antipodes), or as mixtures of optical isomers such as racemates, or as mixtures of geometric isomers.

In case geometric or diastereomeric mixtures of the above compounds or intermediates are obtained, these can be separated into the single racemic or optically active isomers by methods in themselves known, e.g. by fractional distillation crystallization and/or chromatography.

The racemic products of formula I or basic intermediates can be resolved into the optical antipodes, for example, by separation of diastereomeric salts thereof, such as according to J. Org. Chem. 43, 3803 (1978), e.g., by the fractional crystallization of d- or l-(tartrate, mandelate or camphorsulfonate) salts.

Any acidic intermediates can be resolved by separation of e.g. the d- and l-($\alpha$-methylbenzylamine, cinchonidine, cinchonine, quinine, quinidine, ephedrine, dehydroabietylamine, brucine or strychnine)-salts of any compounds having an acidic salt-forming group.

Advantageously, the more active of the antipodes of the compounds of this invention is isolated.

Finally, the compounds of the invention are either obtained in the free form, or as a salt thereof. Any resulting base can be converted into a corresponding acid addition salt, preferably with the use of a pharmaceutically acceptable acid or anion exchange preparation, or resulting salts can be converted into the corresponding free bases, for example, with the use of a stronger base, such as a metal or ammonium hydroxide, or any basic salt, e.g., an alkali metal hydroxide or carbonate, or a cation exchange preparation. These or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

The compounds, including their salts, can also be obtained in the form of their hydrates, or include other solvents used for the crystallization.

The present invention additionally relates to the compounds of the formula I and their pharmaceutically acceptable, non-toxic acid addition salts for use as medicaments, especially as serotonin uptake inhibitors, e.g. as psychotropic agents, particularly antidepressant agents, for example for the treatment of endogenous depression and other diseases responsive to serotonin uptake inhibition, and especially for their use for the preparation of pharmaceutical compositions, especially compositions having serotonin-uptake inhibiting activity, particularly antidepressant activity.

The pharmaceutical compositions according to the invention are those suitable for enteral, such as oral or rectal, and parenteral administration to mammals, including man, for the treatment or prevention of diseases responsive to e.g. the inhibition of central neuronal serotonin uptake, e.g. central nervous system diseases such as depression, comprising an effective amount of a pharmacologically active compound of formula I, or pharmaceutically acceptable salts thereof, alone or in combination with one or more pharmaceutically acceptable carriers.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with (a) diluents, e.g. lactose, dextrose, sucrose, mannitol, sorbitol, cellulose and/or glycine; (b) lubricants, e.g. silica, talcum, stearic acid, its magnesium or calcium salt and/or polyethyleneglycol; for tablets also (c) binders, e.g. magnesium aluminum silicate, starch paste, gelatin, tragacanth, methylcellulose, sodium carboxymethylcellulose and/or polyvinylpyrrolidone; if desired, (d) disintegrants, e.g. starches, agar, alginic acid or its sodium salt, or effervescent mixtures; and/or (e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating osmotic pressure and/or buffers. In addition, the compositions may also contain other therapeutically valuable substances. Said compositions are prepared according to conventional mixing, granulating or coating methods, respectively and contain about 0.1 to 75%, preferably about 1 to 50%, of the active ingredient.

More specifically, the invention relates advantageously to the method of treatment of psychotropic disorders, especially depression, using the compounds of the formula I or pharmaceutically acceptable, non-toxic salts of such compounds as pharmacologically active substances, especially as anti-depressant agents, preferably in the form of above-cited pharmaceutical compositions. The dosage of active compound administered is dependent on the species of warm-blooded animal, the body weight, age and individual condition, and on the form of administration.

A unit dosage for a mammal of about 50 to 70 kg may contain between about 10 and 100 mg of the active ingredient.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg.

EXAMPLE 1

A mixture of 2-benzyl-3-dimethylaminopropanol (4.2 g), dicyclohexylcarbodiimide (4.6 g) and cuprous chloride (0.2 g) is maintained at 80° for 40 hours. 4-Trifluoromethylphenol (5.0 g) is added, and the mixture maintained at 130° for 12 hours. The reaction mixture is cooled and ether (100 ml) is added. The insoluble material is filtered off and the filtrate extracted with 2N hydrochloric acid (3×100 ml). The acidic solutions are combined and made basic by the addition of concentrated aqueous ammonia. The aqueous solution is extracted with ether (3×150 ml), and the combined extracts dried over magnesium sulfate and evaporated under reduced pressure to give the ether as a yellow oil. This material is converted to the oxalate salt by dissolving in ether and adding the calculated quantity of oxalic acid dihydrate in ether. Filtration gives N,N-dimethyl-2-benzyl-3-(4-trifluoromethylphenoxy)-propylamine oxalate, m.p. 147°–149°.

The starting material is prepared as follows:

A solution of 30.0 g of methyl α-benzylacrylate, prepared by the method of R. B. Miller and B. F. Smith, Synth. Commun. 3, 359 (1973) in methanol (50 ml) is added to a solution of dimethylamine (71.0 g) in methanol (210 ml), and the mixture is stirred at room temperature for 48 hours. The solvent is removed under reduced pressure to give methyl 2-benzyl-3-dimethylaminopropionate as a yellow oil, used without purification in the next synthetic step; NMR: $\delta$7.14 (s, 5H), 3.52 (s, 3H), 2.82 (m, 3H), 2.17 (s, 6H), 2.63–2.17 (m, remaining H).

A solution of methyl 2-benzyl-3-dimethylaminopropionate (60.0 g) in ether (300 ml) is added dropwise with stirring under a nitrogen atmosphere to a suspension of lithium aluminum hydride (28.0 g) in ether (700 ml). The reaction mixture is refluxed for 4 hours, then stirred at room temperature for 18 hours. The reaction mixture is cooled to 0°, and water (30 ml) is added cautiously (dropwise initially) followed by 10% NaOH (60 ml). The solid inorganic material is filtered off, and the filtrate dried over magnesium sulfate. The solvent is removed under reduced pressure to give 2-benzyl-3-dimethylaminopropanol as an oil which is used without further purification; NMR(CDCl$_3$): $\delta$7.12 (m, 5H), 5.62 (broad s, 1H), 3.57 (m, 2H).

EXAMPLE 2

A mixture of 2-(3-chlorobenzyl)-3-dimethylaminopropanol (5 g), 4-methylmercaptophenol (3.3 g), and dicyclohexylcarbodiimide (4.5 g) is maintained at 180° for 72 hours. The reaction mixture is cooled to room temperature and ether (100 ml) and 1N hydrochloric acid (120 ml) are added. The layers are separated and the aqueous solution is extracted with more ether (100 ml), made basic by the addition of concentrated ammonia, and extracted with ether (2×100 ml). These latter combined ether solutions are dried over potassium carbonate, and the solvent removed under reduced pressure. Treatment of the resulting oil with oxalic acid in ether yields N,N-dimethyl-2-(3-chlorobenzyl)-3-(4-methylmercaptophenoxy)-propylamine oxalate, m.p. 122°–124°.

EXAMPLE 3

The following compounds of formula I, isolated and characterized as the oxalate salt are prepared essentially according to the procedures illustrated in Examples 1 and 2 (Me=methyl; Ph=phenyl).

| Ex. | $R_1$ | $R_2$ | $R_3$ | Ar | X | m.p. (°C.) of oxalate salt |
|---|---|---|---|---|---|---|
| 3/1 | Me | Me | H | 3-OMe—Ph | O | 85–88 (dec) |
| 3/2 | Me | Me | H | 4-SMe—Ph | O | 128–130 |
| 3/3 | Me | Me | H | 2-Cl—Ph | O | 91–93 (dec) |
| 3/4 | Me | Me | H | 4-Cl—Ph | O | 133–136 (dec) |
| 3/5 | —(CH$_2$)$_5$— | | H | 4-OMe—Ph | O | 139–141 |
| 3/6 | Me | Me | H | 3-Cl—Ph | O | 112–114 |
| 3/7 | Me | Me | H | 4-Me—Ph | O | 115–117 |
| 3/8 | Me | Me | H | 3-Me—Ph | O | 94–97 |
| 3/9 | Me | Me | H | 4-OMe—Ph | S | 124–127 |
| 3/10 | Me | Me | H | 3-CF$_3$—Ph | O | 97–99 |
| 3/11 | Me | Me | H | 3-OMe—Ph | S | 94–97 |

-continued

| Ex. | $R_1$ | $R_2$ | $R_3$ | Ar | X | m.p. (°C.) of oxalate salt |
|---|---|---|---|---|---|---|
| 3/12 | Me | Me | H | 3,5-di-OMe—Ph | O | 106–108 |
| 3/13 | Me | Me | H | 3-(OCH$_2$CH=CH$_2$)—Ph | O | 110–112 |
| 3/14 | Me | Me | 4-Cl | 4-SMe—Ph | O | 114–116 |
| 3/15 | Me | Me | 3-Cl | 4-CF$_3$—Ph | O | 138–140 |
| 3/16 | Me | Me | H | 4-OMe—Ph | O | 108–111 |

The novel starting materials are prepared as follows:

(a) Ethyl α-(chlorobenzyl)acrylates are prepared as described below:

A solution of potassium hydroxide (26 g) in absolute ethanol (375 ml) is added during 30 minutes to an ice-cold solution of diethyl 3-chlorobenzylmalonate (112 g) in absolute ethanol (375 ml). The solution is stirred at room temperature for 18 hours, and the solvent removed under reduced pressure. The residue is dissolved in water (1200 ml) and the solution cooled in an ice-bath. Concentrated hydrochloric acid (29 ml) is added, and the solution extracted with ether (2×350 ml). The combined ether solutions are washed with water (250 ml), dried over magnesium sulfate, and evaporated under reduced pressure to give as an oil, 3-chlorobenzylmalonic acid monoethyl ester; NMR (CDCl$_3$)δ: 10.13 (s, 1H), 7.2 (m, 4H), 4.15 (q, 2H), 3.5 (m, 3H), 1.21 (t, 3H).

Diethylamine (27.6 g, 39 ml) is added dropwise with shaking to 3-chlorobenzylmalonic acid monoethyl ester (90.0 g) [Chem. Ber. 92, 203 (1959)], in a flask cooled in a water bath. Aqueous formaldehyde (37%, 38 ml) is added dropwise with shaking and cooling as before. Gas is evolved, and the reaction mixture becomes lighter in color. The mixture is stirred at room temperature for 65 hours, then water (500 ml) is added, and the solution extracted with ether (2×350 ml). The combined ether solutions are washed with water (300 ml), 3N HCl (2×200 ml) and water (300 ml). The ether solution is dried over magnesium sulfate, and the solvent removed under reduced pressure to give ethyl α-(3-chlorobenzyl)acrylate as a yellow oil, NMR (CDCl$_3$)δ: 7.15 (m, 4H), 6.22 (s, 1H), 5.45 (m, 1H), 4.13 (q, 2H), 3.58 (s, 2H), 1.23 (t, 3H).

Ethyl α-(4-chlorobenzyl)acrylate is prepared by a similar procedure starting with diethyl 4-chlorobenzylmalonate (J. Med. Chem. 17, 732 (1974); NMR (CDCl$_3$)δ: 7.15 (m, 4H), 6.17 (s, 1H), 5.38 (m, 1H), 4.11 (q, 2H), 3.55 (s, 2H), 1.20 (t, 3H).

(b) The following esters are prepared essentially according to the method illustrated in Example 1 under the reaction conditions indicated.

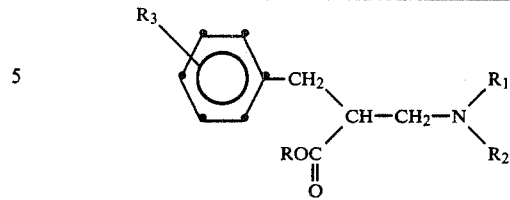

| $R_1$ | $R_2$ | $R_3$ | R | Reaction Conditions |
|---|---|---|---|---|
| —(CH$_2$)$_5$— | | H | Me | Refluxing methanol, 18 hours |
| Et | Me | H | Me | Refluxing methanol, 6 days |
| PhCH$_2$ | Me | H | Me | Refluxing methanol, 4 weeks |
| Me | Me | 4-Cl | Et | Methanol, room temperature, 18 hours |
| Me | Me | 3-Cl | Et | Methanol, room temperature, 24 hours |
| H | Me | H | Me | Methanol, room temperature, 48 hours |

(c) The following alcohols are prepared essentially according to the method illustrated in Example 1.

| $R_1$ | $R_2$ | $R_3$ | NMR (δ, For OH) |
|---|---|---|---|
| —(CH$_2$)$_5$— | | H | 5.8 |
| Et | Me | H | 6.1 |
| PhCH$_2$ | Me | H | 5.0 |
| Me | Me | 4-Cl | 5.6 |
| Me | Me | 3-Cl | 5.6 |

EXAMPLE 4

A solution of N-carbethoxy-N-methyl-2-benzyl-3-(4-trifluoromethylphenoxy)propylamine (25.0 g) and potassium hydroxide (25.0 g) in isopropanol (200 ml) is refluxed for 48 hours. The reaction mixture is cooled to room temperature, and the solvent removed under reduced pressure. Water (250 ml) is added, and the mixture extracted with dichloromethane (2×150 ml). The combined dichloromethane solutions are washed with water (150 ml), dried over magnessium sulfate, and the solvent removed under reduced pressure to give an oil. This material is dissolved in ether (500 ml) and dry hydrogen chloride is bubbled in until no further precipitation occurs. The solid is filtered off, washed with ether (250 ml) and dried to give N-methyl-2-benzyl-3-(4-trifluoromethylphenoxy)propylamine hydrochloride, mp 161°–162°, the compound of formula I wherein $R_1$ is methyl, $R_2$ and $R_3$ are hydrogen and Ar is 4-trifluoromethylphenyl. The oxalate salt, prepared in the standard way, has m.p. 173°–175°.

The starting material is prepared as follows:

A solution of N,N-dimethyl-2-benzyl-3-(4-trifluoromethylphenoxy)propylamine (22.0 g) and ethyl chloroformate (34.1 g, 30.0 ml) in dry toluene (200 ml) is refluxed for 72 hours. The reaction mixture is cooled to room temperature, and the solvent removed under reduced pressure. Water (200 ml) is added, and the mixture extracted with dichloromethane (2×150 ml). The combined dichloromethane extracts are washed with 2N hydrochloric acid (200 ml) and water (200 ml), and dried over magnesium sulfate. The solvent is removed under reduced pressure to give N-carbethoxy-N-methyl-2-benzyl-3-(4-trifluoromethylphenoxy)- propylamine as an oil, which is used without purification for the next synthetic step above.

EXAMPLE 5

A solution of N-benzyl-N-methyl-2-benzyl-3-(3-methoxyphenoxy)propylamine (7.0 g) in ethanol (100 ml) is hydrogenated at room temperature and atmospheric pressure until uptake ceases, using 10% palladium on charcoal (2.0 g) as catalyst. The catalyst is filtered off (Hi-flo) and the solvent removed under reduced pressure to give N-methyl-2-benzyl-3-(3-methoxyphenoxy)propylamine as an oil, which is converted with oxalic acid in ether of N-methyl-2-benzyl-3-(3-methoxyphenoxy)propylamine oxalate, m.p. 127°–129° C.

The starting material as the oxalate salt, prepared by procedure of example 2, has melting point of 79°–81°.

EXAMPLE 6

The following compounds of formula I wherein $R_2$ represents hydrogen and X represents O, isolated and characterized as the oxalate salt, are prepared similarly to the compounds of examples 4 and 5 essentially according to the procedures described therein (Me=methyl, Ph=phenyl)

| Example | $R_1$ | $R_3$ | Ar | m.p. (°C.) of oxalate salt |
|---|---|---|---|---|
| 6/1 | Me | H | 4-OMe—Ph | 142–144 |
| 6/2 | Me | H | 4-SMe—Ph | 172–174 |
| 6/3 | Me | 3-Cl | 4-SMe—Ph | 177–179 |

A starting material for example 6/1 is N,2-dibenzyl-N-methyl-3-(4-methoxyphenoxy)propylamine oxalate, m.p. 147°–9°.

EXAMPLE 7

Sodium hydride (4.2 g of 50% mineral oil dispersion) is washed with petroleum ether (3×100 ml) and dried under a stream of dry nitrogen. Dimethylformamide (65 ml, dried with 4A molecule sieves) is added. A solution of 2-benzyl-3-dimethylaminopropanol (14 g) in dry dimethylformamide (30 ml) is added with stirring. Stirring is maintained for 10 minutes at room temperature, and then at 55° for 1 hour. A solution of 4-fluorobenzotrifluoride (12.0 g) in dry dimethylformamide (25 ml) is added dropwise, and the reaction mixture is stirred at 60° for 6 hours, and then at room temperature for 18 hours. Water (300 ml) is added, and the solution extracted with ether (2×200 ml). The combined ether solutions are extracted with 3N hydrochloric acid (2×150 ml). The combined acidic extracts are washed with ether (200 ml), and made basic by the addition of concentrated aqueous ammonia. The aqueous solution is extracted with ether (2×250 ml), and the combined ether solutions washed with water (100 ml), and dried over magnesium sulfate. The solvent is removed under reduced pressure to give N,N-dimethyl-2-benzyl-3-(4-trifluoromethylphenoxy)propylamine, identical to the compound of Example 1, which may be converted to N,N-dimethyl-2-benzyl-3-(4-trifluoromethylphenoxy)propylamine oxalate as described in Example 1.

EXAMPLE 8

A mixture of 10% palladium on charcoal (2.0 g) and N,N-dimethyl-2-benzyl-3-(2-methoxyphenoxy)propylamine (2 g from oxalate salt melting at 76°–79° dec.) in methanol (300 ml) is stirred at room temperature in an open flask for 18 hours. The catalyst is filtered off and the solvent removed under reduced pressure. The residual oil is converted with an equivalent amount of oxalic acid in ether to N-methyl-2-benzyl-3-(2-methoxyphenoxy)propylamine oxalate, m.p. 135°–139°.

EXAMPLE 9

(a) A solution of N-methyl-N-acetyl-2-benzyl-3-(4-methylthiophenoxy)propylamine (12.6 g) in dry ether (100 ml) is added dropwise to a stirred suspension of lithium aluminum hydride (4.0 g) in dry ether (250 ml). The reaction mixture is refluxed for 18 hours, and cooled to 0°. Water (3 ml) is added cautiously, followed by 15% sodium hydroxide (3 ml), and water (9 ml). The inorganic salts are filtered off, washed with ether (150 ml) and the combined ether solutions are dried over magnesium sulfate. The solvent is removed under reduced pressure to give N-methyl-N-ethyl-2-benzyl-3-(4-methylthiophenoxy)propylamine.

The starting material is prepared as follows: Treatment of N-methyl-2-benzyl-3-(4-methylthiophenoxy)propylamine with acetyl chloride at room temperature in dichloromethane in the presence of triethylamine yields N-methyl-N-acetyl-2-benzyl-3-(4-methylthiophenoxy)propylamine.

EXAMPLE 10

A solution of N,N-dimethyl-2-benzyl-3-(4-methylthiophenoxy)propylamine (3.0 g) in methanol (350 ml) is added dropwise under nitrogen during 30 minutes to a solution of sodium periodate (4.8 g) in water (160 ml). After the addition is complete, the reaction mixture is stirred at room temperature for 4 hours, added to water (500 ml) and extracted with ether (2×250 ml). The combined ether solutions are dried over potassium carbonate, and the solvent removed under reduced pressure to give an oil. Treatment with an equivalent amount of oxalic acid in ether followed by recrystallization of the resulting salt from methanol/ether (3×) gives N,N-dimethyl-2-benzyl-3-(4-methylsulfinylphenoxy)propylamine oxalate, m.p. 112°–115°.

EXAMPLE 11

Compounds of the previous examples are tested for their ability to block the uptake of tritiated serotonin into synaptosomal nerve endings from rat whole brain in vitro essentially by the method of Thornburg and Moore as described in Res. Comm. Chem. Pathol. Pharmacol. 5, 81 (1973). The preincubation period of the test compound (added in ethanol solution) with the whole brain synaptosome suspension in Krebs buffer is 5 minutes. The incubation period, following the addition of tritiated serotonin ($^3$H-5-HT) to a final concentration of about $1 \times 10^{-7}$M, is 4 minutes. The concentration of test agent required to inhibit serotonin uptake by 50% of control value i.e. the IC$_{50}$, is determined graphically and expressed in micromolar concentration. The concentration of test agent required to inhibit norepinephrine (NE) uptake by 50% of the control value, i.e., the IC$_{50}$ is similarly determined using tritiated norepinephrine ($^3$H-NE) and is also expressed in micromolar concentration.

| Compound of Example | 5-HT Uptake Inhibition IC$_{50}$ ($\mu$M) | NE Uptake Inhibition IC$_{50}$ ($\mu$M) |
| --- | --- | --- |
| 1 | 0.49 | 15.25 |
| 2 | 0.03 | 5.0 |
| 3/1 | 0.43 | 4.3 |
| 3/2 | 0.27 | 10.8 |
| 3/3 | 1.3 | 5.3 |
| 3/4 | 1.49 | 12.0 |
| 3/5 | 6.1 | 39.5 |
| 3/6 | 2.7 | 16.1 |
| 3/7 | 1.22 | 12.5 |
| 3/8 | 1.25 | 3.25 |
| 3/9 | 1.53 | 8.1 |
| 3/10 | 2.25 | 6.9 |
| 3/11 | 1.95 | 7.6 |
| 3/12 | 1.52 | 4.3 |
| 3/13 | 0.59 | 1.44 |
| 3/14 | 0.67 | 7.1 |
| 3/15 | 6.0 | 32.0 |
| 3/16 | 0.56 | 0.57 |
| 4 | 0.39 | 12.6 |
| 5 | 0.94 | 1.39 |
| 6/1 | 0.44 | 1.25 |
| 6/2 | 0.14 | 2.5 |
| 6/3 | 2.7 | 11.0 |
| 8 | 5.4 | 8.9 |

EXAMPLE 12

Preparation of 10,000 tablets each containing 10 mg of the active ingredient of Example 4:

| Formula: | |
| --- | --- |
| N—Methyl-2-benzyl-3-(4-trifluoromethylphenoxy)-propylamine hydrochloride | 100.00 g |
| Lactose | 1,157.00 g |
| Corn Starch | 75.00 g |
| Polyethylene glycol 6,000 | 75.00 g |
| Talcum powder | 75.00 g |
| Magnesium stearate | 18.00 g |
| Purified water | q.s. |

Procedure:

All the powders are passed through a screen with openings of 0.6 mm. Then the drug substance, lactose, talcum, magnesium stearate and half of the starch are mixed in a suitable mixer. The other half of the starch is suspended in 40 ml of water and the suspension added to the boiling solution of the polyethylene glycol in 150 ml of water. The paste formed is added to the powders which are granulated, if necessary, with an additional amount of water. The granulate is dried overnight at 35°, broken on a screen with 1.2 mm openings and compressed into tablets using concave punches with 6.4 mm diameter, uppers bisected.

EXAMPLE 13

Preparation of 10,000 capsules each containing 25 mg of the active ingredient of Example 4:

| Formula: | |
| --- | --- |
| N—Methyl-2-benzyl-3-(4-trifluoromethylphenoxy)-propylamine hydrochloride | 250.0 g |
| Lactose | 1,650.0 g |
| Talcum powder | 100.0 g |

Procedure:

All the powders are passed through a screen with openings of 0.6 mm. Then the drug substance is placed in a suitable mixer and mixed first with the talcum, then with the lactose until homogeneous. No. 3 capsules are filled with 200 mg, using a capsule filling machine.

Analogously tablets or capsules are prepared from the remaining compounds of the invention, e.g., those illustrated by the examples herein.

EXAMPLE 14

The intermediate methyl 2-benzyl-3-dimethylaminopropionate (see example 1) is also advantageously prepared as follows:

Liquid dimethylamine (500 g) is added to 1800 ml of methanol cooled to −35°. A solution of 500 g of methyl acrylate in 850 ml of methanol is then added keeping the temperature between −50° and −60°. The reaction mixture is kept at −50° to −60° for 2½ hours and then at room temperature overnight. The solvent is removed in vacuo and the residue is distilled under reduced pressure to give methyl 3-dimethylaminopropionate b.p. 60°−70°/16 mm Hg.

A solution of 101 g of diisopropylamine in 200 ml of tetrahydrofuran is cooled to −78° under nitrogen. 2.1M n-butyllithium in tetrahydrofuran (470 ml) is added dropwise keeping the temperature at −78°.

The reaction mixture is stirred for ½ hour at the same temperature, a solution of 179 g of hexamethylphosphoramide in 200 ml of tetrahydrofuran is added and stirring is continued for ½ hour at −78°. At the same temperature a solution of 125 g of methyl N,N-dimethylaminopropionate in 200 ml of tetrahydrofuran is then added dropwise and stirring is continued for 20 minutes. A solution of 171 g of benzyl bromide in 300 ml of tetrahydrofuran is then added, again at −78°. The solution is stirred at this temperature for 2 hours and then quenched, first with 250 ml of saturated aqueous ammonium chloride and then 250 ml of saturated aqueous sodium chloride solution. To this is added 1500 ml of ether. The layers are separated and the aqueous layer is extracted with 4×200 ml of ether. The ether extract is dried over magnesium sulfate and evaporated to dryness. The resulting oil is redissolved in 300 ml of ether, the ether solution is washed with 100 ml of water and the aqueous layer is reextracted with 3×100 ml ether. The combined ether solutions are dried over magnesium sulfate and evaporated to dryness in yield an oil which is purified by fractional distillation to yield pure methyl 2-benzyl-3-dimethylaminopropionate, b.p. 104°/0.2–0.4 mm Hg.

EXAMPLE 15

Condensation of benzylmagnesium bromide with N,N,-diethyl-3-phenoxy-2-chloropropylamine (the method disclosed in French patent application No. 2,148,001 or e.g. the substantially equivalent British Application No. 1,343,527 for the preparation of compounds therein) yields a product consisting predominantly of compound characterized by NMR spectroscopy as 1-phenoxymethyl-3-phenyl-N,N-diethylpropylamine. The compound of the structure actually depicted for compound No. 60 in said patent publication is only detected as a minor side-product of the condensation (by comparison of the reaction product using thin-layer chromatography with N,N-diethyl-2-benzyl-3-phenoxypropylamine prepared unambiguously as described in example 16).

Thin-layer chromatography (TLC) system: Methanol, ethyl acetate (3:1) as eluent on silica gel plates.

EXAMPLE 16

A mixture of 2-benzyl-3-diethylaminopropanol (8.0 g), dicyclohexylcarbodiimide (7.5 g) and cuprous chloride (0.2 g) is maintained at 80° for 48 hours. Phenol (4.6 g) is added and the mixture maintained at 120° for 65 hours. The reaction mixture is cooled, ether (200 ml) added and the resulting solid filtered off. The ether solution is extracted with 3N hydrochloric acid (2×100 ml) and the combined acidic solutions are washed with ether (300 ml) and made basic by the addition of aqueous ammonia. The basic solution is extracted with ether (2×150 ml) and the combined ether solutions washed with water (100 ml), and dried over potassium carbonate. Hydrogen chloride gas is bubbled through the solution and the resulting gum is washed and triturated with ether. The resulting solid is recrystallized from ethyl acetate to give N,N-diethyl-2-benzyl-3-phenoxypropylamine hydrochloride, m.p. 122°–124°.

The structure is confirmed by NMR spectroscopy. This compound is not identical to the major product of the condensation of benzylmagnesium bromide with N,N-diethyl-3-phenoxy-2-chloropropylamine but is only detected as a minor side-product thereof (see above example 15).

The starting 2-benzyl-3-diethylaminopropanol is obtained by addition of diethylamine to methyl 2-benzylacrylate and subsequent reduction according to the procedure described in example 1.

The serotonin uptake inhibitory activity of N,N-diethyl-2-benzyl-3-phenoxypropylamine hydrochloride is evaluated with the following results in the tests indicated.

(a) Uptake inhibition in synaptosomes from rat whole brain according to example 11.

IC$_{50}$ for serotonin uptake inhibition = 7.3×10$^{-6}$M (or 7.3 μM)

IC$_{50}$ for norepinephrine uptake inhibition = 3.3×10$^{-6}$M (or 3.3 μM)

(b) Inhibition of the serotonin-depleting effect of H 75/12 in H 75/12 test in the rat: 17% inhibition at 30 mg/Kg p.o.

(c) Uptake inhibition in synaptosomes from rat midbrain-diencephalon region.

IC$_{50}$ for serotonin uptake inhibition = 2.2×10$^{-6}$M (or 2.2 μM)

IC$_{50}$ for norepinephrine uptake inhibition = 2.0×10$^{-6}$M (or 2.0 μM)

The data serves to demonstrate that N,N-diethyl-2-benzyl-3-phenoxypropylamine hydrochloride shows no significant in vivo serotonin uptake inhibitory activity in the rat at 30 mg/Kg p.o. Furthermore, no selectivity is seen in in vitro tests.

What is claimed is:

1. A compound having the formula

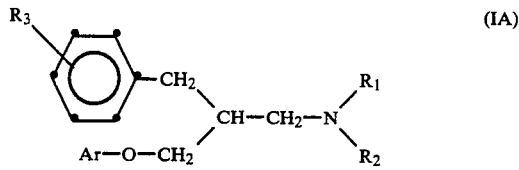

wherein R$_1$ represents hydrogen or methyl; R$_2$ represents methyl; R$_3$ represents hydrogen; and Ar represents 4-trifluoromethylphenyl; or a pharmaceutically acceptable salt thereof.

2. A compound of claim 1 being N,N-dimethyl-2-benzyl-3-(4-trifluoromethylphenoxy)propylamine or a pharmaceutically acceptable acid addition salt thereof.

3. A compound of claim 1 being N-methyl-2-benzyl-3-(4-trifluoromethylphenoxy)propylamine or a pharmaceutically acceptable salt thereof.

4. An antidepressant pharmaceutical composition comprising an effective amount of a serotonin uptake inhibiting compound of claim 1 in combination with one or more pharmaceutical carriers.

5. A pharmaceutical composition according to claim 4 wherein the compound is N-methyl-2-benzyl-3-(4-trifluoromethylphenoxy)propylamine or a pharmaceutically acceptable salt thereof.

6. A method of treating mammals suffering from depression which comprises administering to said mammal in need thereof an effective amount of a serotonin uptake inhibiting compound of claim 1 in combination with one or more pharmaceutical carriers.

7. A method according to claim 6 wherein the compound is N-methyl-2-benzyl-3-(4-trifluoromethylphenoxy)-propylamine or a pharmaceutically acceptable salt thereof.

* * * * *